(12) United States Patent
Ballevre et al.

(10) Patent No.: US 7,794,744 B2
(45) Date of Patent: Sep. 14, 2010

(54) NUTRITIONAL MODULES

(75) Inventors: Olivier Ballevre, Lausanne (CH); Julio Boza, Granada (ES); Denis Breuille, Saint-Saturnin (FR); Paul-André Finot, St-Legier (CH); Véronique Jaussan, Morges (CH); Claudia Roessle, Morges (CH); Thomas Schweizer, Le Mont-sur-Lausanne (CH)

(73) Assignee: Nestec S.A., Vevey (CH)

( * ) Notice: Subject to any disclaimer, the term of this patent is extended or adjusted under 35 U.S.C. 154(b) by 1147 days.

(21) Appl. No.: 10/257,208

(22) PCT Filed: Apr. 3, 2001

(86) PCT No.: PCT/EP01/03790

§ 371 (c)(1),
(2), (4) Date: Feb. 21, 2003

(87) PCT Pub. No.: WO01/78533

PCT Pub. Date: Oct. 25, 2001

(65) Prior Publication Data

US 2003/0161863 A1   Aug. 28, 2003

(30) Foreign Application Priority Data

Apr. 18, 2000   (EP) ................... 00108412

(51) Int. Cl.
*A61K 47/00* (2006.01)
(52) U.S. Cl. ...................................... 424/439
(58) Field of Classification Search ............... 424/439
See application file for complete search history.

(56) References Cited

U.S. PATENT DOCUMENTS

| 4,871,550 | A | 10/1989 | Millman |
| 5,332,579 | A | 7/1994 | Umbdenstock |
| 5,438,042 | A | 8/1995 | Schmidl et al. |
| 5,550,146 | A | 8/1996 | Acosta et al. |
| 5,733,884 | A | 3/1998 | Barbul et al. |
| 5,973,224 | A | 10/1999 | Fuchs et al. |

FOREIGN PATENT DOCUMENTS

| EP | 0 861 654 A1 | 9/1998 |
| EP | 861 654 | * 9/1998 |
| EP | 0 891 719 A1 | 1/1999 |
| EP | 0 904 784 A1 | 3/1999 |
| FR | 2 623 394 | 5/1989 |
| GB | 2 323 030 A | 9/1998 |
| WO | WO 91/11117 | 8/1991 |

OTHER PUBLICATIONS

Eileen et al (Accuracy of enteral pumps: In vitro performance, J. of Parenteral and Enteral Nutrition, 18(4), p. 359-361, 1994) ABS.*

* cited by examiner

*Primary Examiner*—Alton N Pryor
(74) *Attorney, Agent, or Firm*—Gary M. Lobel

(57) ABSTRACT

The present invention relates to a method for preparing an enteral nutrition at the bed of a patient, which involves the use of a standard enteral solution to which is added, via a closed system, one or more compositions in module form, containing selected nutrients, adapted for a specific clinical condition. The present invention also pertains to the different modules, that are preferably in dry form and to the use thereof in the treatment and/or nourishment of a critically ill person.

21 Claims, No Drawings

NUTRITIONAL MODULES

The present invention relates to a method for preparing an enteral nutrition at the bed of a patient, which involves the use of a standard enteral solution to which is added, via a closed system, one or more compositions in module form, containing selected nutrients, adapted for a specific clinical condition. The present invention also pertains to the different modules, that are preferably in dry form and to the use thereof in the treatment and/or nourishment of a critically ill person.

Many patients in a critically ill condition have to be fed via the enteral route, which involves the use of special nutrition in liquid form, supplied to the patient via a tube directly into the stomach. Enteral formulations include a variety of different substances, such as proteins respectively amino acids, carbohydrates, lipids etc., that is compounds known to provide a nutritional value to an individual, but also substances beneficial to the well being or recovery of an individual, such as e.g. vitamins. Yet, a problem involved in providing these formulation resides in that some substances are not stable in liquid when stored for a prolonged period of time or must be submitted to heat treatment during the manufacturing process.

Enteral formulations are occasionally provided in dry form, to be supplemented with water. After dissolving or suspending the powder in the liquid, the formulation may be administered to the patient. Though formulations in dry form have an advantage that even compounds, known to be unstable in liquids, may be included as such, the addition of water on-site, i.e. in the hospital or at the bed of the patient poses problems as regards a potential contamination of the formulation by pathogens. In fact, the water utilized for this purpose on-site does either not meet the safety standards or due to the handling in mixing the water with the powder contamination occurs. Since an enteral formulation provides all nutrients for growth of pathogens, micro-organisms once entered said formulation will rapidly grow and may represent a danger for the patient. For this reason, dry formulations to be supplemented by water are not popular.

Another option to provide enteral formulations resides in using ready-to-use formulations that had been manufactured under essentially aseptic conditions in the factory and that are provided in a bag to be connected with the feeding system. These formulations contain a predetermined composition of basic nutrients, occasionally supplemented with one or the other substance known to promote an individual's recovery.

However, it has been shown that in the clinical course of a patient, the nutritional requirements of a patient are subject to changes, so that a patient will exhibit a demand for a specific substance, beneficial for overcoming a particular stress situation only at a distinct stage of his recovery. In consequence, the nutritional needs of a critically ill patient are not constant over time, but change quite rapidly during the early phase and become more constant in a clinically stable patient.

Presently available formulations cannot cope with such changing needs of a patient, since they represent ready-to-use formulations containing predetermined ingredients. What is more, due to the fact that the presently sold, ready-to-use formulations contain predetermined ingredients, they regularly do not supply a patient with all of the different nutritional ingredients he requires. For this reason a number of different ready-to-use nutritional formulations have been designed which meet the requirements of some disease conditions. Yet, up to now, there is not enteral formulation in the art that may cope with all of a patient's demand and in addition considers the changing nutritional needs of a patient.

Therefore, a need exists for an appropriate course of nutrition, which addresses the changing nutritional needs of a patient and simultaneously avoids contamination of the enteral formulation by micro-organisms.

The above problem has been solved by a method for preparing an enteral food material at the bed of a critically ill person which comprises, (i) providing a standard enteral formulation and (ii) adding to this standard enteral formulation via a closed system one or more compositions in a module form, containing selected nutrients, adapted for a specific clinical condition.

Within the context of this invention the term "standard enteral formulation" comprises any standard enteral diet, such as e.g. the commercially available diet, that contains amounts of proteins and/or peptides and/or carbohydrates and/or lipids, normally included in such diets. Examples of tube-feeding diets are e.g. NUTREN®, NUTREN® VHP, SONDALIS®, SONDALIS HP®, PEPTAMEN®, PEPTAMEN 1.5®, PEPTAMEN VHP®, REABILAN® or REABILAN HN®, examples for oral diets are the ranges of CLINUTREN® and NUBASICS® products, respectively.

The term "module" represents a nutritional composition for addressing one or more clinical symptom(s), such as e.g. oxidative stress or an hypermetabolic "flow phase" after injury, packaged in a form, allowing a direct introduction of the module ingredients into the standard nutrient solution, such as e.g. in a bag or in the apparatus described in EP 0 861 654, the contents of which is incorporated herein by way of reference.

The term "critically ill" encompasses a wide variety of pathologies including, but not limited to multiple trauma, severe head injury, burns or sepsis/SIRS (systemic inflammatory response syndrome), major surgery or aquired respiratory distress syndrome (ARDS).

Consequently, in a first aspect the present invention provides for a method for preparing an enteral formulation directly at the bed of the patient via a closed system. The enteral formulation can rapidly and easily be adapted to the different nutritional needs of a patient during the clinical course, i.e. during the different stages after a major adverse event for the body. Thus it becomes possible to deliver a specific nutrient to a patient at a specific time during the clinical course of recovery.

The composition of the module is preferably mixed with the standard enteral formulation via the system described in EP 0 861 654, the contents of which is incorporated herein by way of reference.

Further, the ingredients of the modules are preferably present in dry form, which allows a long storability also of components, that are not stable in liquids. With the system described in EP 0 851 654 it is possible to mix the ingredients of one or more module(s) without contact with the environment, so that a potential contamination of the enteral formulation may be avoided. In addition, one of the most immanent advantages of the present invention may be seen in that the enteral formulation to be administered to a patient will always be exact the formulation, the patient is in need of and which has not been contaminated with micro-organisms due to a handling by the attending personal or contact with the environment, such as exposure to air. In addition also a storage problem may be avoided. Nowadays many different enteral formulations have to be stored in hospitals to provide different nutritional sources. According to the present invention only a standard solution is required, which is then supplemented at the bed of a patient with the respective module ingredients. Since the module as such does not require much storage space, resources may be saved.

The clinical conditions a patient may be subjected during his clinical course of recovery are e.g. (a) oxidative stress, (b)

hypermetabolism, (c) systemic inflammatory syndrome (SIRS) (d) wound healing, (e) acquired respiratory distress syndrome (ARDS), (f) bone trauma or (g) a reduced, modified, or pathogen-containing gut's microflora.

According to a preferred embodiment the substances against an oxidative stress condition are selected from compounds having anti-oxidative activity and/or precursors thereof and/or glutamine, preferably from compounds selected from the group consisting of glutamine, cysteine and precursors or derivatives thereof (acetylcysteine, procysteine, methionine, cystine), vitamin E, vitamin C, β-carotene and/or precursors thereof, zinc and selenium.

According to another preferred embodiment the substances for limiting hypermetabolism and muscle wasting of the patient are selected from the group comprising glutamine, cysteine and precursors or derivatives thereof (acetylcysteine, procysteine, methionine, cystine), threonine, aspartate, serine and/or precursors thereof.

According to another preferred embodiment the substances for assisting wound healing are selected from the group comprising specific amino acids (arginine, proline, hydroxyproline, glutamine, glycine), milk-derived or recombinant growth factors (for example transforming growth factor β-2), bioactive peptides, probiotic bacteria and/or their metabolites, selected micronutrients (zinc, selenium, copper), antioxidant vitamins (Vitamins A, E, C, carotenoids), other vitamins (Folic acid, vitamin B12), flavonoids, lycopene, fatty acids which modify the inflammatory response (eicosapentaenoic acid, arachidonic acid, alpha-linolenic acid, gamma-linolenic acid).

According to yet another preferred embodiment the substances to effect an acquired respiratory distress syndrome (ARDS) and other acute inflammatory conditions (systemic inflammatory response syndrome=SIRS) comprise selected micronutrients (zinc, selenium, copper), antioxidant vitamins (Vitamins A, E, C, carotenoids) cysteine and precursors or derivatives thereof (acetylcysteine, procysteine, methionine, cystine), flavonoids, lycopene, fatty acids with antinflammatory action (eicosapentaenoic acid, alpha-linolenic acid, gamma-linolenic acid), milk-derived or recombinant growth factors with anti-inflammatory properties such as transforming growth factor β2.

According to still another preferred embodiment the substances against bone trauma comprise calcium, preferably a milk calcium source, vitamin D and/or its precursors, selected electrolytes and minerals (magnesium, zinc, sodium, potassium, chloride, manganese, fer, iodine, chromium, copper, molybdenium), selected vitamins (Vitamins A, E, C, K1, B1, B2, B6, Niacin, Folic acid, B12, Biotin), isoflavones, milk-derived or recombinant bioactive peptides and growth factors (for example casein glycomacropeptide, casein, phosphopeptides, osteoprotegerin), prebiotics, preferably selected from the group comprising fructo-oligosaccharides, acacia gum or an oligosaccharide produced from glucose, galactose, xylose, maltose, sucrose, lactose, or starch, xylan, hemicellulose, inulin or a mixture thereof.

According to still another preferred embodiment the substances for reconstituting the gut's microflora comprise probiotics, preferably micro-organisms belonging to the genus *Lactobacillus* and/or *Bifidobacterium*, preferably *Lactobacillus acidophilus* La1 (CNCM I-1225) and *Bifidobacterium longum* ST11 (CNCM I-2170), and/or prebiotics, preferably prebiotics selected from the group comprising fructo-oligosaccharides, acacia gum or an oligosaccharide produse from glucose, galactose, xylose, maltose, sucrose, lactose, or starch, xylan, hemicellulose, inulin or a mixture thereof.

The modules may be utilized in single form, i.e. a module for a specific function, e.g. assisting the patient to better cope with an oxidative stress after surgery, may be admixed with a standard enteral formulation, while at another period during the clinical course another module (directed to a different task, e.g. limiting hypermetabolism and muscle wasting) may be admixed with a different batch of a standard enteral formulation (normally provided in a unit of 500 ml or 1000 ml). Proceeding accordingly is considered to represent a single use of a module.

However, the modules may also be used at the same time, while the contents of two or more modules are admixed with the enteral standard formulation. The method of the present invention enables the attending personal to quickly change the nutritional value and/or composition of an enteral feed depending on the advice of the attending physician taking into account the present status and/or need of the patient. Preferably, the modules may be superposed. i.e. in a given patient and a given day (or a series of days), several different modules can be administered in different amounts independently.

As an example, a plurality of nutritional modules for treatment of a critically ill patient includes a first module, comprising substances against oxidative stress, a second module, comprising substance for limiting hypermetabolism/muscle waste and/or a third module, comprising substances for reconstituting the gut's microflora.

Preferably, the first module comprises three or more nutrients selected from the group which consists of glutamine, cysteine, vitamin E, vitamin C, β-carotene, zinc and selenium. More preferably, it comprises at least five of these nutrients. Most preferably, it comprises all of these nutrients. Preferably, the amounts of these nutrients, if present in the first module, per 500 ml of enteral diet are as follows:

Glutamine: preferably about 5 g to about 10 g, more preferably about 6 g. Glutamine provides the advantage of providing fuel to gastrointestinal and immune cells, in addition it helps avoid early depletion of glutamine, furthermore it helps reduce bacterial translocation and helps prevent muscle loss and improves nitrogen balance.

Cysteine: preferably about 1.5 g to about 5 g, more preferably about 2.5 g. Cysteine provides the advantage of aiding defence against oxidative stress, it is necessary for sustained synthesis of glutathione (a major antioxidant), it provides a synergistic effect for glutamine synthesis and aids synthesis of proteins produced in the acute phase of oxidative stress. Preferably, cysteine can be provided in the form of free cysteine, a dipeptide or polypeptide including cysteine and another amino acid or other amino acids, acetylcysteine, cystine, methionine, procysteine, or a mixture thereof.

Vitamin C: preferably about 120 mg to about 300 mg, more preferably about 140 mg; vitamin E: preferably about 20 mg to about 100 mg, more preferably about 30 mg; β-carotene: preferably about 5 mg to about 10 mg, more preferably about 6 mg. Vitamin C, vitamin E and β-carotene provide the advantage that they are lipo-soluble and water soluble antioxidants, they help meet their enhanced requirement during oxidative stress and they help overcome the problem of their low supply with low volumes of typical nutritional feeds in the early phase after injury/sepsis/burns/surgical intervention when full strength enteral feeding is difficult to achieve.

Zinc: preferably about 5 mg to about 10 mg, more preferably about 6 mg. The presence of zinc provides the advantages that it helps compensate for its increased losses during oxidative stress, it has antioxidant properties, it helps promote synthesis of metallothionein, it is an essential co-factor for protein synthesis and helps improve the function of the immune system.

Selenium: preferably about 40 μg to about 100 μg, more preferably about 50 μg. The presence of selenium provides the advantage that it helps compensate for its increased losses during oxidative stress, it has antioxidant properties and is a co-factor for glutathione peroxidase.

The second module preferably comprises three or more nutrients selected from the group which consists of glutamine, cysteine, threonine, aspartate and serine. More preferably, it comprises all of these nutrients. Preferably, the amounts of these nutrients, if present in the second module, per 500 ml of enteral diet are as follows:

Glutamine: preferably about 5 g to about 10 g, more preferably about 6 g. Glutamine provides the advantage of helping to prevent muscle loss, in addition it helps improve nitrogen balance, it provides fuel to gastrointestinal and immune cells, furthermore it helps reduce bacterial translocation and helps prevent muscle loss and improves nitrogen balance.

Cysteine: preferably about 1.5 g to about 5 g, more preferably about 2.5 g. Cysteine provides the advantage of aiding defence against oxidative stress, it is necessary for sustained synthesis of glutathione (a major antioxidant), it provides a synergistic effect for glutamine synthesis and aids synthesis of proteins produced in the acute phase of oxidative stress. Preferably, cysteine can be provided in the form of free cysteine, a dipeptide or polypeptide including cysteine and another amino acid or other amino acids, acetylcysteine, cystine, methionine, procysteine, or a mixture thereof.

Threonine: preferably about 1.0 g to about 5.0 g, more preferably about 1.5 g. Threonine provides the advantage that it promotes synthesis of proteins produced in the acute phase of oxidative stress and it promotes synthesis of mucoproteins protecting the mucosal surface of the gastrointestinal tract and lungs.

Aspartate: preferably about 1.5 g to about 4 g, more preferably about 1.9 g; Serine: preferably about 4.0 g to about 8.0 g, more preferably about 4.6 g. Aspartate and serine provide the advantage of providing a source of nitrogen for compensating increased losses during critical illness.

Preferably, the third module comprises one or more components selected from the group which consists of a bacterium having probiotic properties and/or a prebiotic selected from the group which comprises fructooligosaccharide (FOS), acacia gum or an oligosaccharide produced from glucose, galactose, xylose, maltose, sucrose, lactose, starch, xylan, hemicellulose, inulin, or a mixture thereof.

Preferably the bacterium having probiotic properties is selected from the group which consists of Lactobacillus acidophilus La1 (CNCM I-1225). Bifidobacteria, ST11 (CNCM I-2170), both of which have been deposited with the Institute Pasteur according to the Budapest Treaty and may be freely obtained therefrom. Preferably, the micro-organisms are present in freeze dried form. In addition, preferably the amount of lactic acid bacterium in the module is $10^8$-$10^{13}$ cfu (colony forming units), more preferably the amount is about $10^{10}$ cfu.

The third module provides the advantage that it promotes the restoration of the intestinal flora often destroyed by an antecedent treatment with antibiotics. In addition, in view of the fact that it preferably includes a "friendly" bacterium, it provides the advantage that it aids prevention of bacterial overgrowth by pathogens. Yet another advantage is that it aids prevention of diarrhoea in a patient and helps to improve the function of their immune system.

According to a preferred embodiment the ingredients of the modules are provided in powder form, so that compounds tending to degrade in liquids, such as glutamine and cysteine, will only be contacted with liquid directly prior to its use. More preferably they are provided in a closed system device. This provides the advantage that they can be added to the enteral diet of a patient in an extemporaneous manner without compromising hygienic safety.

Preferably, the modules are provided to a patient suffering from critical illness in order, starting with module 1 and successively providing module 2, then module 3. More preferably, the modules overlap in their time of use.

Preferably, modules have components in common—i.e. they overlap in their composition because some nutrients may be used to address several symptoms and should not be withdrawn abruptly. This provides the advantage that a smooth transition from treatment with one type of module to treatment with another type of module can be achieved.

Also superposition of the modules is possible, which provides the advantage that a patient's needs may be addressed without safety concerns.

The nutritional modules are enterally administrable, for example in the form of a powder, a liquid concentrate, or for oral intake, for example as a ready-to-drink beverage. The powder or liquid concentrate is added (by using a suitable device, supra) to standard feeding bags or to standard products in cans, bottles, plastic cups or bags. If it is desired to produce a powdered module, the ingredients are first dried (if necessary) e.g. by being transferred to a suitable drying apparatus, such as a spray drier or freeze drier, converted to powder form and dry-mixed. The ingredients of a module are then stored in a container, adapted to allow mixing with the standard enteral formulation without contact with the environment, such as in bags or the apparatus described in EP 0 861 654.

An embodiment of the first module is suitable for nutrition during the early phase of clinical conditions including multiple trauma, head trauma, burns, extensive surgery or sepsis; and the hypermetabolic "flow phase" of a condition after injury. This module may be administered alone or it may be administered during the first three days after injury or sepsis together with a low volume of a high protein or peptide standard enteral diet. For example, a commercially available diet such as NUTREN®, NUTREN® VHP, SONDALIS®, SONDALIS HP®, PEPTAMEN®, PEPTAMEN 1.5®, PEPTAMEN VHP®, REABILAN®, REABILAN HN®, CLINUTREN® or NUBASCIS® may be enriched. Alternatively, it may be administered during the period from about the second to about the tenth day after injury or sepsis together with a typical conventional volume of a high protein or peptide standard enteral diet. The amount of the first module added is preferably at least about 0.01% by weight. Furthermore, it may be administered in combination with parenteral nutrition.

An embodiment of a second module is suitable for nutrition during the hypermetabolic "flow" phase of clinical conditions including multiple trauma, head trauma, burns, extensive surgery or sepsis. This module may be administered alone or it may be administered during the period from about the second to about the tenth day after injury or sepsis together with a typical conventional volume of a high protein or peptide standard enteral diet. For example, a commercially available diet such as NUTREN®, NUTREN® VHP, SONDALIS®; SONDALIS HP®, PEPTAMEN®, PEPTAMEN 1.5®, PEPTAMEN VHP®, REABILAN HN®, CLINUTREN® or NUBASCIS® may be enriched. The amount of the second module added is preferably at least about 0.01% by weight. Furthermore, it may be administered in combination with parenteral nutrition.

An embodiment of a third module is suitable for nutrition during the whole period of critical illness, particularly during and after treatment with antibiotics and in case of diarrhoea. The amount of this module added is preferably enough to provide at least $10^8$ cfu of bacteria, more preferably at least $10^{10}$ cfu of bacteria. According to yet another preferred embodiment a module of the present invention consists of (a) a first module which consists of at least one component having anti-oxidative activity and/or precursors thereof and/or glutamine, and (b) a second module, which consists of at least one component limiting hypermetabolism/muscle waste of the patient, and optionally including ordinary carriers and/or excipients.

The following examples are given by way of illustration only and in no way should be construed as limiting the subject matter of the present application. Percentages and parts are by weight unless otherwise indicated.

EXAMPLE 1

A First Module

An embodiment of a first module was produced by blending the following nutrients in the required amounts. Its composition is indicated below:

| Nutrient | Quantity |
| --- | --- |
| Glutamine | 6 g |
| Cysteine | 2.5 g |
| Vitamin E | 30 mg |
| Vitamin C | 140 mg |
| β-carotene | 6 mg |
| Zinc | 6 mg |
| Selenium | 50 μg |

Administration of this module can be superposed with administration of another module. I.e. in a given patient and a given day, several different modules can be administered in different amounts independently. Furthermore, the module can be administered a number of times per day. For example, it can be administered once per day. Alternatively, it can be administered more than once per day, for example about 3 to about 5 times per day. Of course, it can be administered in less or greater amounts depending on the needs of a patient and combined with various volumes of the standard enteral feed which are usually dispatched in units of 500 ml or 1000 ml.

EXAMPLE 2

A Second Module

An embodiment of a second module was produced by blending the following nutrients in the required amounts. Its composition is indicated below:

| Nutrient | Quantity |
| --- | --- |
| L-Glutamine | 6 g |
| L-Cysteine | 2.5 g |
| L-Threonine | 1.5 g |

-continued

| Nutrient | Quantity |
| --- | --- |
| L-Aspartate (eg in form of sodium aspartate) | 1.9 g |
| L-Serine | 4.6 g |

Administration of this module can be superposed with administration of another module. I.e. in a given patient and a given day, several different modules can be administered in different amounts independently. Furthermore, the module can be administered a number of times per day. For example, it can be administered once per day. Alternatively, it can be administered more than once per day, for example about 3 to about 5 times per day. Of course, it can be administered in less or greater amounts depending on the needs of a patient and combined with various volumes of the standard enteral feed which are usually dispatched in units of 500 ml or 1000 ml.

EXAMPLE 3

A Third Module

An embodiment of a third module was produced by blending the following nutrients in the required amounts. Its composition is indicated below:

| Nutrient | Quantity |
| --- | --- |
| Lactic acid bacterium La1 | $10^{10}$ cfu |

Administration of this module can be superposed with administration of another module. I.e. in a given patient and a given day, several different modules can be administered in different amounts independently. Furthermore, the module can be administered a number of times per day. For example, it can be administered once per day. Alternatively, it can be administered more than once per day, for example about 3 to about 5 times per day. Of course, it can be administered in less or greater amounts depending on the needs of a patient and combined with various volumes of the standard enteral feed which are usually dispatched in units of 500 ml or 1000 ml.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:

1. A process for preparing an enteral food material at a location of a critically ill person comprising the steps of:
   (i) providing a standard enteral formulation,
   (ii) adding to the standard enteral formulation via a closed system a therapeutically effective amount of at least two compositions, each composition being packaged in a separate module and containing selected nutrients chosen for a specific clinical condition, adding the compositions in a manner selected from the group consisting of additions of multiple modules at the same time, overlapping additions of multiple modules, and additions of multiple modules in sequence, to flexibly address changing patient nutritional needs.

2. The process according to claim 1, wherein the compositions to be added to the standard formulation are in dry form.

3. The process according to claim 1, wherein the composition is selected from the group consisting of compounds having anti-oxidative activity, glutamine, cysteine, vitamin E, vitamin C, β-carotene, zinc and selenium.

4. The process according to claim 1, wherein the composition is selected from the group consisting of glutamine, cysteine, threonine, aspartate, and serine.

5. The process according to claim 1, wherein the composition is selected from the group consisting of arginine, proline, hydroxyproline, glutamine, glycine, milk-derived or recombinant growth factors, bioactive peptides, probiotic bacteria, zinc, selenium, copper, antioxidant vitamins, folic acid, vitamin B12, carotenoids, flavonoids, lycopene, eicosapentaenoic acid, arachidonic acid, alpha-linolenic acid, and gamma-linolenic acid.

6. The process according to claim 1, wherein the composition is selected from the group consisting of zinc, selenium, copper, Vitamins A, E, C, carotenoids, cysteine and precursors or derivatives, flavonoids, lycopene, eicosapentaenoic acid, alpha-linolenic acid, gamma-linolenic acid, milk-derived and recombinant growth factors with anti-inflammatory properties such as transforming growth factor β2.

7. The process according to claim 1, wherein the composition is selected from the group consisting of calcium, vitamin D, magnesium, zinc, sodium, potassium, chloride, manganese, fer, iodine, chromium, copper, molybdenium, Vitamins A, E, C, K1, B1, B2, B6, Niacin, Folic acid, B12, Biotin, isoflavones, milk-derived or recombinant bioactive peptides and growth factors, fructo-oligosaccharides, acacia gum, an oligo-saccharide produced from glucose, galactose, xylose, maltose, sucrose, lactose, starch, xylan, hemicellulose, inulin and mixtures thereof.

8. The process according to claim 1, wherein the composition is selected from the group consisting of probiotics and prebiotics, including micro-organisms belonging to the genus *Lactobacillus* and *Bifidobacterium*, and *Lactobacillus acidophilus* La1 (CNCM I-1225) and *Bifidobacterium longum* ST11 (CNCM I-2170), and wherein the prebiotic is selected from the group consisting of fructo-oligosaccharide, acacia gum, an oligo-saccharide produced from glucose, galactose, xylose, maltose, sucrose, lactose, or starch, xylan, hemicellulose, inulin and mixtures thereof.

9. The process according to claim 1, wherein two or more modules are added to the standard enteral formula sequentially.

10. A process according to claim 1, wherein two or more modules are added to a standard enteral formula at the same time.

11. A method for treating a critically ill patient comprising the steps of:
adding to a standard enteral formula at a location of a patient at least two separate packaged modules containing different components, in a manner selected from the group consisting of additions of multiple modules at the same time, overlapping additions of multiple modules, additions of multiple modules in sequence, the components being designed to treat at least one condition the critically ill patient exhibits or suffers from.

12. A method according to claim 11, wherein the module to be added to the standard formulation is in dry form.

13. A method according to claim 11, wherein the components are selected from the group consisting of compounds having anti-oxidative activity, glutamine, cysteine, vitamin E, vitamin C, β-carotene, zinc and selenium.

14. A method according to claim 11, wherein the components are selected from the group consisting of glutamine, cysteine, threonine, aspartate, and serine.

15. A method according to claim 11, wherein the components for assisting wound healing are selected from the group consisting of arginine, proline, hydroxyproline, glutamine, glycine, milk-derived or recombinant growth factors, bioactive peptides, probiotic bacteria, zinc, selenium, copper, antioxidant vitamins, folic acid, vitamin B12, carotenoids, flavonoids, lycopene, and eicosapentaenoic acid, arachidonic acid, alpha-linolenic acid, and gamma-linolenic acid.

16. A method according to claim 11, wherein the components are selected from the group consisting of zinc, selenium, copper, Vitamins A, E, C, carotenoids, cysteine, flavonoids, lycopene, eicosapentaenoic acid, alpha-linolenic acid, gamma-linolenic acid, milk-derived and recombinant growth factors with anti-inflammatory properties.

17. A method according to claim 11, wherein the components are selected from the group consisting of calcium, vitamin D, magnesium, zinc, sodium, potassium, chloride, manganese, fer, iodine, chromium, copper, molybdenium, Vitamins A, E, C, K1, B1, B2, B6, Niacin, Folic acid, B12, Biotin, isoflavones, milk-derived or recombinant bioactive peptides and growth factors, fructo-oligosaccharides, acacia gum and an oligosaccharide produced from glucose, galactose, xylose, maltose, sucrose, lactose, starch, xylan, hemicellulose, inulin and mixtures thereof.

18. A method according to claim 11, wherein the components are selected from the group consisting of probiotics and prebiotics, including micro-organisms belonging to the genus *Lactobacillus* and *Bifidobacterium*, and *Lactobacillus acidophilus* La1 (CNCM I-1225) and *Bifidobacterium longum* ST11 (CNCM I-2170), and wherein the prebiotic is selected from the group consisting of fructo-oligosaccharide, acacia gum, an oligosaccharide produced from glucose, galactose, xylose, maltose, sucrose, lactose, or starch, xylan, hemicellulose, inulin and mixtures thereof.

19. A method according to claim 11, wherein two or more modules are added to the standard enteral formula sequentially.

20. A method according to claim 11, wherein two or more modules are added to the standard enteral formula at the same time.

21. A method of preparing a therapeutic composition for a critically ill patient comprising the steps of:
providing a standard enteral formulation, and
(ii) adding to the standard enteral formulation via a closed system at least two compositions, each composition being packaged in a separate module form and containing selected nutrients chosen for a specific clinical condition, adding the compositions in a manner selected from the group consisting of additions of multiple modules at the same time, overlapping additions of multiple modules, additions of multiple modules in sequence, to flexibly address changing patient nutritional needs.

* * * * *